US010149641B2

(12) United States Patent
O'Malley et al.

(10) Patent No.: US 10,149,641 B2
(45) Date of Patent: Dec. 11, 2018

(54) SYSTEMS, METHODS, AND DEVICES FOR REDUCING THE PAIN OF GLUCOSE MONITORING AND DIABETES TREATMENT

(71) Applicant: Innova Medical Design, LLC, Plymouth, MN (US)

(72) Inventors: Timothy O'Malley, Plymouth, MN (US); Rommel P. Vallero, Davis, CA (US)

(73) Assignee: Innova Medical Design, LLC, Plymouth, MN (US)

( * ) Notice: Subject to any disclaimer, the term of this patent is extended or adjusted under 35 U.S.C. 154(b) by 648 days.

(21) Appl. No.: 14/623,185

(22) Filed: Feb. 16, 2015

(65) Prior Publication Data

US 2015/0157250 A1 Jun. 11, 2015

Related U.S. Application Data

(62) Division of application No. 13/227,223, filed on Sep. 7, 2011.

(60) Provisional application No. 61/497,662, filed on Jun. 16, 2011, provisional application No. 61/380,409, filed on Sep. 7, 2010.

(51) Int. Cl.
| | |
|---|---|
| *A61B 5/15* | (2006.01) |
| *A61B 5/157* | (2006.01) |
| *A61B 5/151* | (2006.01) |
| *A61M 5/42* | (2006.01) |

(52) U.S. Cl.
CPC ........ *A61B 5/150137* (2013.01); *A61B 5/151* (2013.01); *A61B 5/157* (2013.01); *A61B 5/150022* (2013.01); *A61B 5/15186* (2013.01); *A61B 5/150358* (2013.01); *A61B 5/150954* (2013.01); *A61M 5/422* (2013.01); *A61B 5/15109* (2013.01); *A61B 5/15113* (2013.01); *A61B 5/150778* (2013.01); *A61B 5/150793* (2013.01); *A61B 5/150961* (2013.01)

(58) Field of Classification Search
CPC . A61B 5/150022; A61B 5/15186; A61B 5/15; A61B 5/157; A61B 5/150137; A61M 5/422
See application file for complete search history.

(56) References Cited

U.S. PATENT DOCUMENTS

| | | | | |
|---|---|---|---|---|
| 5,752,512 A | * | 5/1998 | Gozani | A61B 5/05 600/347 |
| 6,183,489 B1 | * | 2/2001 | Douglas | A61B 5/14532 600/583 |
| 6,332,871 B1 | * | 12/2001 | Douglas | A61B 5/14532 600/583 |
| 8,702,624 B2 | * | 4/2014 | Alden | A61B 5/15113 600/583 |
| 9,333,144 B2 | * | 5/2016 | Baxter | A61H 23/00 |
| 9,636,051 B2 | * | 5/2017 | Emery | A61B 5/14532 |
| 9,757,059 B2 | * | 9/2017 | Hoenes | A61B 5/1459 |

(Continued)

*Primary Examiner* — Sean Dougherty
(74) *Attorney, Agent, or Firm* — Davis, Brown, Koehn, Shors & Roberts, P.C.; Sean D. Solberg

(57) ABSTRACT

The various embodiments disclosed herein are devices that deliver electrical stimulation and/or vibration stimulation to the surface of skin in proximity to insulin injections and/or glucose testing in order to decrease or eliminate the pain of these procedures.

27 Claims, 8 Drawing Sheets

(56) References Cited

U.S. PATENT DOCUMENTS

| | | | |
|---|---|---|---|
| 2002/0130042 A1* | 9/2002 | Moerman | A61B 5/1486 204/403.01 |
| 2004/0267299 A1* | 12/2004 | Kuriger | A61B 5/15186 606/181 |
| 2005/0177071 A1* | 8/2005 | Nakayama | A61B 5/150122 600/583 |
| 2007/0083131 A1* | 4/2007 | Escutia | A61B 5/1411 600/583 |
| 2008/0077048 A1* | 3/2008 | Escutia | A61B 5/1411 600/583 |
| 2009/0054811 A1* | 2/2009 | Boecker | A61B 5/14532 600/583 |
| 2009/0112123 A1* | 4/2009 | Freeman | A61B 5/1411 600/583 |
| 2010/0261988 A1* | 10/2010 | Tamir | A61B 5/14546 600/365 |
| 2010/0274181 A1* | 10/2010 | Wang | G01N 27/3273 604/66 |
| 2010/0280348 A1* | 11/2010 | Wenzel | A61B 5/0452 600/365 |
| 2011/0105872 A1* | 5/2011 | Chickering, III | A61B 5/157 600/365 |
| 2011/0144463 A1* | 6/2011 | Pesach | A61B 5/14532 600/345 |
| 2011/0178434 A1* | 7/2011 | Jacobs | A61B 5/15186 600/583 |
| 2012/0271123 A1* | 10/2012 | Castle | A61B 5/150022 600/309 |
| 2014/0364767 A1* | 12/2014 | Terashima | A61B 5/1411 600/583 |
| 2017/0173262 A1* | 6/2017 | Veltz | A61M 5/1723 |

* cited by examiner

SYSTEMS, METHODS, AND DEVICES FOR REDUCING THE PAIN OF GLUCOSE MONITORING AND DIABETES TREATMENT

CROSS-REFERENCE TO RELATED APPLICATION(S)

This application claims priority as a divisional of U.S. patent application Ser. No. 13/227,223, filed Sep. 7, 2011 and entitled "Systems, Methods, and Devices for Reducing the Pain of Glucose Monitoring and Diabetes Treatment," which claims the benefit under 35 U.S.C. § 119(e) to U.S. Provisional Patent Application 61/380,409, filed Sep. 7, 2010, entitled "Systems and Methods for Reducing the Pain of Glucose Monitoring and Insulin Administration in Diabetic Patients," and to U.S. Provisional Patent Application 61/497,662, filed Jun. 16, 2011, entitled "Devices, Systems, and Methods for Reducing the Pain of Glucose Monitoring and Insulin Administration in Diabetic Patients," all of which are hereby incorporated herein by reference in their entireties.

FIELD OF THE INVENTION

The embodiments disclosed herein relate to various methods and devices for reducing or eliminating pain of injections and other similar procedures performed on the skin, including the pain associated with blood glucose testing and insulin shot administration. Certain implementations relate to methods or devices that deliver stimulation in the form of vibration, electrical stimulation, or both to the patient.

BACKGROUND OF THE INVENTION

Diabetic patients often have to check their blood glucose levels multiple times per day. This is most commonly done using a sharp lancet device to create a small pinprick on a fingertip or other body part from which a drop of blood may be obtained for sampling. In addition, many diabetics require multiple daily doses of insulin given subcutaneously (typically in the abdominal wall, thighs or arms) in order to keep their blood sugars at a safe level. It has been shown that a significant number of diabetics are non-compliant with their diabetes treatment regimen mainly because of the pain involved. (Burge, Diabetes Care, August 2001, vol. 24, no. 8, 1502-1503) This noncompliance has been shown to double the risk of hospitalization in these patients resulting in almost double the medical costs. (Sokol, *Medical Care*, June 2005, Volume 43, Issue 6, pp: 521-530)

There is a need in the art for improved systems, methods, and devices for reducing or eliminating pain from injections and related procedures for treating diabetes.

BRIEF SUMMARY OF THE INVENTION

Discussed herein are various embodiments relating to methods, devices, and systems for reducing or eliminating pain related to treatment of diabetes, including pain from blood glucose testing and from treatment injections (such as, for example, insulin injections). The various embodiments include pain reduction or elimination using either electrical or vibration stimulation, or both. More specifically, certain embodiments relate to handheld devices that provide pain reduction in combination with either blood testing or treatment injections or both. Further embodiments relate to handheld devices that provide pain reduction for use with other commercially-available blood testing and diabetes treatment devices.

In Example 1, a combination blood testing and pain reduction device comprises a body, a lancet housing, a lancet, a first stimulation component, and a stimulation generating unit. The lancet housing is disposed at a distal end of the body and comprises an opening disposed at a distal end of the lancet housing. The lancet is disposed at least partially within the lancet housing and comprises a retracted position disposed within the lancet housing and a deployed position wherein at least a distal portion of the lancet extends out of the lancet housing through the opening. The first stimulation component is coupled to the distal end of the lancet housing and comprises an electrode configured to be capable of delivering at least one of electrical stimulation and vibration stimulation. The stimulation generating unit is disposed within the body and is configured to transmit at least one of electrical energy and vibration energy to the first stimulation component.

Example 2 relates to the device according to Example 1, and further comprising a controller operably coupled to the stimulation generating unit, the controller configured to control the stimulation generating unit.

Example 3 relates to the device according to Example 1, wherein the first stimulation component is a positionable stimulation component movably coupled to the distal end of the lancet housing. The positionable stimulation component is configured to be movable between a testing configuration and an administration configuration. Further, the positionable stimulation component in the testing configuration is positioned against the distal end of the lancet housing, and the positionable stimulation component in the administration configuration has a portion positioned away from the distal end of the lancet housing. In addition, the stimulation component in the administration configuration has a stimulation component opening defined in the stimulation component.

Example 4 relates to the device according to Example 1, wherein the first stimulation component is positioned against the distal end of the lancet housing and disposed at least partially around the opening in the lancet housing.

Example 5 relates to the device according to Example 1, wherein the first stimulation component comprises a removable stimulation component. The removable stimulation component comprises a removable testing stimulation component and a removable administration stimulation component. The removable testing stimulation component is coupleable with the distal end of the lancet housing and is positioned against the distal end of the lancet housing. The removable administration stimulation component is coupleable with the distal end of the lancet housing and has a portion positioned away from the distal end of the lancet housing. Further, the removable administration stimulation component has a stimulation component opening defined in the removable administration stimulation component.

Example 6 relates to the device according to Example 1, wherein the device is at least one of a glucose testing device, an auto lancet, an insulin auto needle injector, or an insulin pen.

Example 7 relates to the device according to Example 1 and further comprises a second stimulation component disposed along a bottom portion of the body.

Example 8 relates to the device according to Example 7 and further comprises a proximal end having a concave shape, whereby an optimal injection site is created by the second stimulation component adjacent to the concave shape of the proximal end.

Example 9 relates to the device according to Example 8 and further comprises a testing strip opening defined in the proximal end of the body, the testing strip opening configured to receive a testing strip.

Example 10 relates to the device according to Example 9 and further comprises a testing component operably coupled to the testing strip opening and a display operably coupled to the testing component.

Example 11 relates to the device according to Example 7, wherein the body comprises a rounded top portion configured to be easily grasped by a patient.

In Example 12, a combination blood testing, treatment administration, and pain reduction device comprises a cylindrical body, a lancet housing disposed at a distal end of the body, a lancet disposed at least partially within the lancet housing, a positionable stimulation component movably coupled to the distal end of the lancet housing, a stimulation generating unit disposed within the body, and a controller operably coupled to the stimulation generating unit. The lancet housing comprises an opening disposed at a distal end of the lancet housing. The lancet comprises a retracted position disposed within the lancet housing and a deployed position wherein at least a distal portion of the lancet extends out of the lancet housing through the opening. The positionable stimulation component comprises an electrode configured to be capable of delivering at least one of electrical stimulation and vibration stimulation, wherein the positionable stimulation component is configured to be movable between a testing configuration and an administration configuration. The positionable stimulation component in the testing configuration is positioned against the distal end of the lancet housing. In addition, the positionable stimulation component in the administration configuration has a portion positioned away from the distal end of the lancet housing, wherein the stimulation component in the administration configuration has a stimulation component opening defined in the stimulation component. The stimulation generating unit is configured to transmit at least one of electrical energy and vibration energy to the positionable stimulation component. The controller is configured to control the stimulation generating unit.

Example 13 relates to the device according to Example 12 and further comprises an actuation button disposed on a proximal end of the body, the actuation button configured to actuate the lancet and the stimulation generating unit.

Example 14 relates to the device according to Example 12, wherein the device is at least one of a glucose testing device, an auto lancet, an insulin auto needle injector, or an insulin pen.

In Example 15, a combination blood testing, treatment administration, and pain reduction device comprises a body, a lancet housing disposed at a distal end of the body, a lancet disposed at least partially within the lancet housing, a first stimulation component coupled to the distal end of the lancet housing, a second stimulation component disposed along a bottom portion of the body, a proximal end having a concave shape, a stimulation generating unit disposed within the body, and a controller operably coupled to the stimulation generating unit. The lancet housing comprises an opening disposed at a distal end of the lancet housing. The lancet comprises a retracted position disposed within the lancet housing and a deployed position wherein at least a distal portion of the lancet extends out of the lancet housing through the opening. The first stimulation component comprises an electrode configured to be capable of delivering at least one of electrical stimulation and vibration stimulation. An optimal injection site is created by the second stimulation component adjacent to the concave shape of the proximal end. The stimulation generating unit is configured to transmit at least one of electrical energy and vibration energy to the first and second stimulation components. The controller is configured to control the stimulation generating unit.

Example 16 relates to the device according to Example 15 and further comprises a first button operably coupled to the controller and the lancet, the first button configured to actuate the first stimulation component and the lancet.

Example 17 relates to the device according to Example 16 and further comprises a second button operably coupled to the controller, the second button configured to actuate the second stimulation component.

Example 18 relates to the device according to Example 15 and further comprises a testing strip opening defined in the proximal end of the body, the testing strip opening configured to receive a testing strip.

Example 19 relates to the device according to Example 18 and further comprises a testing component operably coupled to the testing strip opening and a display operably coupled to the testing component.

Example 20 relates to the device according to Example 15, wherein the body comprises a rounded top portion configured to be easily grasped by a patient.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The various embodiments disclosed herein are systems, devices, and methods using electrical and/or vibration stimulation to reduce or eliminate pain associated with needles or any other medical devices that pierce the skin of a patient. More specifically, the implementations include hand held systems or devices and related methods using electrical and/or vibration stimulation for reducing pain associated with glucose monitoring and diabetes treatment injections such as insulin injections. Certain device or system embodiments disclosed herein are configured to be used by a patient for self-monitoring and self-injection to reduce or eliminate pain associated with diabetes treatment.

It is understood that electrical stimulation as described herein includes, but is not limited to, transcutaneous electrical nerve stimulation ("TENS"). It is further understood that the most common diabetes treatment is insulin injections. However, the various embodiments disclosed herein are not so limited, and are intended to encompass any other type of diabetes treatment as well, including any other type of drug that could be used instead of or in addition to insulin.

Figure 1:
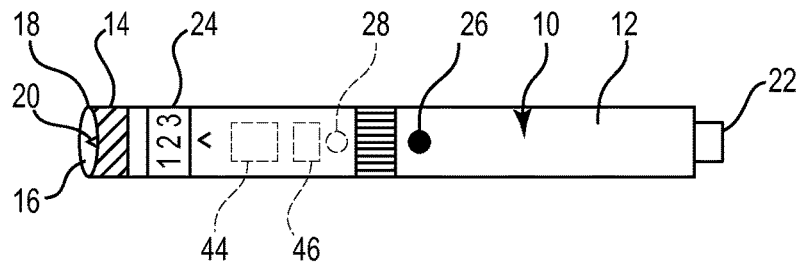
FIG. 1 is a side view of a pain reduction device, according to one embodiment.

FIG. 1 depicts a combination blood glucose testing and pain reduction device 10, according to one embodiment. The device 10 has a cylindrically-shaped body 12 and a removable lancet housing 14 removably coupled at the distal end of the body 12 that defines an opening 16. The opening 16 provides access to an interior portion of the body 12. The removable lancet housing 14 has a stimulation component 18 coupled to a distal portion of the lancet housing 14. The device 10 also has a lancet 20 disposed within the lancet housing 14 (and, in some embodiments, disposed within the body 12 as well) such that it is accessible via the opening 16. That is, the lancet 20 is configured to move between a retracted position within the lancet housing 14 and an deployed position such that a distal portion of the lancet 20 is projecting distally out of the opening 16. The device 10 also has a stimulation energy source unit (depicted schematically as 44) disposed within the body 12 that is operably coupled to the stimulation component 18. The device 10 also has a actuation button 22 (also known as a "plunger" or "plunger button") disposed at the proximal end of the device. The button 22 can be actuated by a user—such as the patient—to move the lancet 20 (or lancets) between the retracted position and the extended position and further to actuate the stimulation unit to deliver stimulation to the stimulation component 18.

In certain embodiments, the device 10 can also have a controller (depicted schematically as 46) disposed within the body 12 to control the delivery of stimulation to the patient and—in some embodiments—to control the lancet 20 as well. Alternatively, the controller can be an integral component of the stimulation energy source unit 44 or otherwise disposed therein. The controller 46 can be any microprocessor, including any programmable microprocessor. For example, the controller 46 can be similar to that found in many commercially available digital devices. In one embodiment, the controller 46 is coupled to any actuation button, such as actuation button 22 and further is coupled to both the stimulation energy source unit 44 and the lancet 20.

In one embodiment, the controller 46 can be pre-programmed to gradually increase either electrical or vibration stimulation or both from a predetermined minimal level to a predetermined maximum level, thereby preventing an initial surprise associated with a more sudden application of full electrical and/or vibration stimulation.

In a further embodiment, the controller 46 can be coupled to the button 22 and any other buttons and can be programmed to deliver varying levels of electrical or vibration stimulation or both based on patient input via the button 22 or any other buttons. For example, the patient in one embodiment can control the level of stimulation based on the amount that the button 22 is depressed. This transmits a signal to the controller 46 that results in actuation of the stimulation energy source unit 44 to generate the corresponding level of stimulation. In this embodiment, the button 22 can be a pressure sensitive button that the patient can use to turn the device 10 on and off and further use to control the intensity of the stimulation, such as, for example, increasing the electrical stimulation current within a range of about 0-80 mA. Alternatively, the device 10 can have one or more additional buttons—such as low, medium, and high intensity buttons—that can be pressed by the patient to transmit a signal to the controller 46 to control the level of stimulation intensity.

In yet another embodiment, the controller 46 can be programmed to provide for the stimulation component to be actuated to deliver stimulation to the patient for some predetermined period prior to actuating the lancet 20 to pierce the skin. Alternatively, the controller 46 can be programmed such that when the user begins to press the button 22, the stimulation component 18 is actuated, but not the lancet 20. As a specific example, when the button 22 has been depressed less than 50% of the full possible amount it can be depressed, the controller 46 only actuates the stimulation component 18, and not the lancet 20. Once the button 22 has been depressed more than 50% of the full amount it can be depressed, both the stimulation component 18 and lancet 20 are actuated. Alternatively, any known mechanism can be used for ensuring that the stimulation component 18 is actuated before the lancet 20 pierces the skin. Regardless of the exact configuration, this feature makes it possible for the electrical and/or vibration stimulation to begin to be delivered before the lancet 20 pierces the skin, thereby providing maximum pain reduction.

In some embodiments described herein, the controller 46 is also responsible for controlling other functions of the device. These variations are discussed in more detail below.

The stimulation energy source unit 44 is configured to generate electrical and/or vibration stimulation that can be delivered as stimulation via the stimulation component 18 to the skin of the patient. In one embodiment, the stimulation component 18 is an electrode and vibration component 18 configured to deliver either electrical or vibration energy or both. Alternatively, the stimulation component 18 is an electrode 18 configured to deliver solely electrical energy. In a further alternative, the stimulation component 18 is a vibration component 18 configured to deliver solely vibration energy.

In one embodiment, the stimulation energy source unit 44 is a separate electronic device that is designed to be operably coupled to the stimulation component via any of various possible known coupling means that allow the transmission of either electrical (including, for example, TENS) or vibration stimulation (or both) to the stimulation component. According to one implementation, the stimulation energy source unit 44 has circuitry typical to that found in commercially-available electrical units for generating electrical stimulation. For example, this circuitry can have the ability to generate electrical stimulation such as single or multiple frequency TENS stimulation and deliver this current to the stimulation component in parallel or in series. For example, in one embodiment, the stimulation energy source unit 44 has electronic circuitry typically found in commercially-available handheld battery-operated TENS devices producing bi-phasic square waves with output currents ranging from about 0 to 80 mA into a 500 Ohm load, which, in some embodiments, can vary depending on user-selected settings. In certain embodiments, such components can also deliver a variable pulse rate (ranging from about 2 Hz-150 Hz) and a variable pulse width (ranging from about 30 microseconds-260 microseconds), again dependent in some implementations on user settings. It is understood that variables such as frequency, current intensity, pulse width, and the like may be user adjustable using any adjustment mechanism as described herein.

For embodiments in which the stimulation energy source unit 44 generates vibration stimulation, either in addition to or instead of electrical stimulation, the unit has a vibration generation component. This component can be any component having rotational or oscillating vibration devices, including commercially-available devices. For example, in one embodiment, the vibration generation component can be any offset weight electrical vibration motor found in any commercially-available cell phone or pager. According to various implementations, the stimulation energy source unit 44 can have one or more vibration generation component, depending on the application. Alternatively, in embodiments providing both electrical and vibration stimulation, the two components can be separate components disposed within the body 12 of the device 10.

It is further understood that the stimulation energy source unit 44 can be any electrical and/or vibration unit disclosed in U.S. application Ser. No. 12/017,324, filed on Jan. 21, 2008, or any such unit disclosed in U.S. application Ser. No. 13/091,753, filed on Apr. 21, 2011, both of which are hereby incorporated herein by reference in their entireties, and can have any of the same features or functionality as those disclosed therein. For example, as discussed in U.S. application Ser. No. 12/017,324, in one embodiment, the stimulation energy source unit 44 can have more than one electrical generation component. Combining the output of two or more electrical generation components could result in more effective reduction of pain. For example, in one of the embodiments disclosed in the '324 Application, the electronic circuitry found in three commercially-available TENS devices are combined and set to produce outputs of 25 Hz, 50 Hz and 110 Hz, all at 180 microseconds. The outputs of these electronic circuits are combined in parallel, resulting in a complex electrical waveform which is a summation of the three combined waveforms. creating a more random feel to the resultant electrical stimulation, which serves to help reduce the user's perception of pain of a lancet or needle stick.

In the embodiment depicted in FIG. 1, the stimulation component 18 is an electrode and vibration component 18 shaped as a ring 18 that is coupled to the distal portion of the removable lancet housing 14 such that the ring 18 encircles the opening 16 through which the retractable lancet 20 moves from its retracted position to its deployed position. The stimulation component 18 is configured to deliver either electrical or vibration stimulation or both. In one embodiment, the stimulation component 18 has at least 2 conductive surfaces, each of which is isolated from the other. The conductive surfaces are used to deliver electrical stimulation.

In the embodiment depicted in FIG. 1, the device body 12 is configured with size, structure, and dimensions that are similar to a standard, commercially-available auto lancet device used for blood glucose testing. Alternatively, the device can have any known configuration that allows for blood glucose testing and incorporates a stimulation energy source unit 44 associated with the body and includes a stimulation component at the distal end of the device.

In certain alternative implementations, the device 10 does not have a removable lancet housing. Instead, the body 12 has a lancet housing at the distal end of the body 12 such that the body 12 has an opening defined at its distal end that provides access to an internal portion of the body 12. In this embodiment, the lancet 20 is configured to move between a retracted position within the non-removable lancet housing and an deployed position such that a distal portion of the lancet 20 is projecting distally out of the opening at the distal end of the body 12.

In certain implementations, the device 10 has an adjustable dial 24 that allows a user to set the level of stimuli. In further embodiments, the device 10 can have an on/off (or "actuation") button 26 to activate the stimulation energy source unit 44. According to one embodiment, the adjustable dial 24 and actuation button 26 are both positioned on the body 12 of the device 10 as shown in FIG. 1. Alternatively, the dial and button can be positioned in any known configuration on the device 10. In one embodiment, the device 10 can also have an indicator light 28 that indicates when the stimulation energy source unit 44 has been activated and turns off after the stimulation energy source unit 44 has been disengaged.

In accordance with one implementation, the stimulation energy source unit 44 is incorporated within the body 12 of the device 10 adjacent to the distal end of the body 12. In this embodiment, the stimulation energy source unit 44 can be connected to the stimulation component 18 by a wire (not shown) or other physical electrical coupling between the removable lancet housing 14 and the coupling component on the distal end of the body 12 that is configured to be coupleable to the lancet housing 14. In one embodiment, the lancet housing 14 and distal end of the body 12 are configured such that the electrical connection is made only when the removable lancet housing 14 is properly affixed to the distal end of the body 12 of the device 10. Alternatively, the stimulation energy source unit 44 can be incorporated into the device 10 in any known fashion or configuration.

In one implementation, the removable lancet housing 14 is configured to be replaceable. That is, the lancet housing 14 can be removed and replaced with another lancet housing 14 if/when the stimulation component 18 on the original lancet housing 14 becomes inoperable, whether as a result of normal wear and tear, damage, or any other reason. In such implementations, the stimulation component 18 can be affixed or coupled to the removable lancet housing 14 such that the lancet housing 14 with the stimulation component 18 can be removed and replaced with another removable lancet housing 14 that has a stimulation component 18. In such embodiments, the stimulation component 18 can be permanently coupled to the lancet housing 14. Alternatively, the stimulation component 18 can be removably coupled to the removable lancet housing 14, such as with an adhesive that allows for the component 18 to be coupled to the lancet housing 14 and further allows for a user to peelably remove the component 18 later. In further alternative embodiments, the stimulation component 18 can be permanently or removably coupled to a distal end of the body 12 of a device 10 that does not have a removable lancet housing.

In certain embodiments, the removable lancet housing 14 is structurally similar to commercially-available removable lancet housings or caps used with many known, commercially-available auto lancet devices. In one embodiment, various versions of the distal lancet housing or cap 14 and the testing device 10 are all configured to have standard coupling components that couple with each other (threads, or any other known coupling components) and are easily reproducible (such as, for example, the standard coupling components used on commercially-available auto lancet devices), thereby allowing for maximum interchangeability of testing devices and removable lancet housings or caps. Alternatively, certain embodiments of the device 10 can have a unique, non-standard coupling component at the distal end of the body 12 such that the device 10 is configured to couple solely to removable lancet housing or cap 14 embodiments having the equivalent coupling component, thereby providing for specifically dedicated removable lancet housings or caps 14 for specific testing devices 10. In a further alternative, the device 10 and lancet housing 14 are configured such that the device 10 will not operate unless the appropriate lancet housing 14 is used. For example, the lancet housing 14 can have a unique configuration that matches the unique configuration of the device 10 such that the coupling of the lancet housing 14 to the device 10 results in the device 10 being operable. In one such example, the lancet housing 14 can have an electrically conductive component such that when the lancet housing 14 is properly coupled to the device 10, the electrically conductive component contacts an appropriate portion of the device 10, thereby closing a circuit that renders the device 10 operable. Alternatively, the lancet housing 14 can have any unique configuration that, when coupled to the device 10 with the matching configuration, results in the closing of a circuit to render the device 10 operable. In one embodiment, this feature can prevent the use of other lancet housings or caps.

According to some embodiments, the lancet 20 (or cartridge of two or more lancets 20) is structurally similar to commercially-available lancets used on many known, commercially-available auto lancet devices. In one implementation, various versions of the lancet 20 (or cartridge) are configured to have a standard configuration that fits within a standard lancet device. Alternatively, certain embodiments of the lancet 20 (or cartridge of lancets) and the device 10 can have a unique configuration such that the lancet 20 (or cartridge) is configured to fit solely within devices 10 having the matching unique configuration, thereby providing for specifically dedicated lancets 20 for specific devices 10.

The various stimulation component 18 implementations having electrode components can include disposable electrodes or multi-use electrodes. In multi-use or reusable electrodes, the non-conductive portions of the electrodes can be made from known, medical grade plastics such as the type used in commercially-available auto lancets. The conductive portions can be made from flexible conductive carbon rubber similar to that used in commercially-available, re-useable TENS electrodes. Alternatively, any known materials that can be used for a multi-use electrode can be used. In disposable electrodes, the non-conductive portions can be made from the same type of plastics described above, while the conductive portions can be created using adhesive biogels or materials similar to that found in commercially available, disposable TENS electrodes. Alternatively, any known materials that can be used for a disposable electrode can be used.

In addition to the ring configuration shown in FIG. 1, the stimulation component 18 can have any known configuration based on the shape of the device to which the component 18 is coupled. In other words, the stimulation component 18 is depicted as a substantially circular ring 18 in FIG. 1 because the distal end of the device 10 is substantially circular. Alternatively, in embodiments in which the distal end is oval in nature, the stimulation component 18 can have a substantially oval shape. In a further alternative, the stimulation component 18 can have an oblong shape to match a distal tip having an oblong shape. According to another alternative, the stimulation component 18 can take on any known shape that matches the shape of the distal end of the body 12, such as square, rectangular, etc. In yet another alternative, the stimulation component 18 can also take on additional configurations that are generally unrelated to the shape of the distal tip. For example, the stimulation component 18 can also have a configuration in which the space defined by the stimulation component 18 is not a hole defined and encircled by the stimulation component 18, but instead is a notch or gap or any other type of space defined by the stimulation component 18, including such spaces that are not fully enclosed by the stimulation component 18. Some examples of such configurations are set forth in U.S. application Ser. No. 12/017,324, filed on Jan. 21, 2008, which is hereby incorporated herein by reference in its entirety.

Figure 2A:
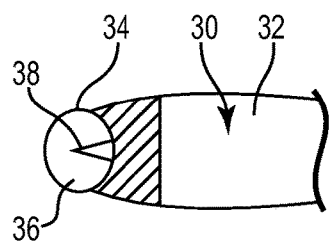
FIG. 2A is a perspective view of a portion of a pain reduction device, according to another embodiment.
Figure 2B:
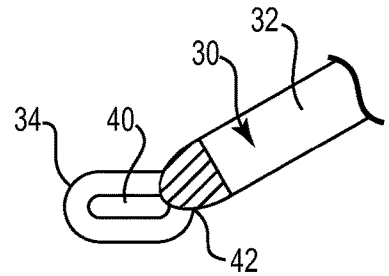
FIG. 2B is a perspective view of a portion of the device of FIG. 2A, according to one embodiment.

FIGS. 2A and 2B depicts a distal portion of an implementation of a combination device 30 that provides for both blood glucose testing and administration of a diabetes treatment such as insulin. The device 30 has a body 32 having a stimulation component 34 coupled to the distal end of the body 32. The stimulation component 34 is disposed around an opening 36 defined in the distal end of the body 32. The device 30 also has a deployable lancet 38 disposed within the body 32 such that it can move between a retracted position within the body 32 and a deployed position in which the lancet 38 extends out of the body 12 through the opening 36.

In this embodiment, the stimulation component 34 can be used to help alleviate pain for either glucose testing or treatment administration. That is, in this embodiment, the stimulation component 34 is configured to move between a glucose testing position as shown in FIG. 2A and a treatment administration position as shown in FIG. 2B. In the glucose testing position as shown in FIG. 2A, the stimulation component 34 is positioned against the distal tip of the device 30 (similar to the embodiment shown in FIG. 1 as well). In this position, the stimulation component 34 is placed in contact with the patient's skin when the distal end of the device 30 is placed against the skin. As such, the stimulation component 34 can apply vibration or electrical stimulation or both to the skin when the lancet 38 is deployed through the distal opening (and thus through the stimulation component ring 34 positioned at the opening 36) and into the skin.

In the treatment administration position as shown in FIG. 2B, the stimulation component 34 is still coupled to the device 30 along at least some portion of the stimulation component 34, but the stimulation component 34 is no longer positioned such that it forms a ring around the distal opening 36 of the device 30. Instead, as shown in FIG. 2B, the stimulation component 34 extends away from the distal end of the device 10 in a fashion that allows the stimulation component 34 to be positioned against the patient's skin while defining an opening 40 within the stimulation component 34 that is accessible by a separate treatment injection device. As such, when the stimulation component 34 is in this administration position, the device 10 can be positioned by the user such that the stimulation component 34 is placed against the patient's skin and a treatment injection needle can be inserted through the stimulation component 34 and into the skin to administer insulin or other treatment substance.

In the embodiment shown in FIGS. 2A and 2B, the stimulation component 34 is hingedly coupled to the distal end of the device 30 with a hinge 42. As shown, the hinge 42 allows the stimulation component 34 to rotatably move between the glucose testing position of FIG. 2A and the treatment administration position of FIG. 2B.

In alternative embodiments, the stimulation component 34 can be configured to move from the testing position to the administration position by pivoting on a rotation point having an axis that is parallel to the longitudinal axis of the testing device 30, by sliding to the side, or by any other known means or configuration.

According to another alternative implementation, instead of a stimulation component 34 that moves between two different positions, the device 30 has two different, interchangeable, removable lancet housings that are coupleable to the distal end of the body 32. One lancet housing is the glucose testing lancet housing and has a stimulation component positioned around the distal opening of the lancet housing such that the lancet moves through the opening in the stimulation component when being deployed out of the distal opening. The other lancet housing is the treatment administration lancet housing and has a stimulation component that extends away from the lancet housing in a fashion similar to that described above and depicted in FIG. 2B such that the stimulation component can be positioned against the skin and allow a treatment injection needle to be inserted into the skin through the opening defined in the stimulation component.

Figure 3:
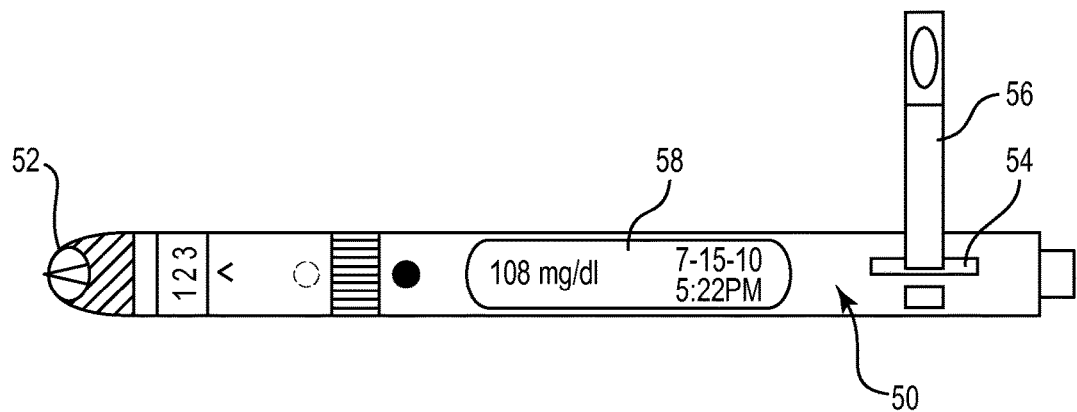
FIG. 3 is a side view of a pain reduction device, according to a further embodiment.

FIG. 3 depicts another embodiment of a combination glucose testing and pain reduction/elimination device 50. The device 50 has many of the same components as the device 10 depicted in FIG. 1, including, for example, a stimulation energy source unit (not shown) and a stimulation component 52. In addition, the device 50 in FIG. 3 also has a glucose test strip receptacle 54 configured to receive a test strip 56, a glucometer (not shown) operably coupled to the receptacle, and a display 58 operably coupled to the glucometer. In one embodiment, the glucometer is disposed within the device 50 and is comprised of electronic circuitry and sensors typically found in commercially-available handheld glucometers. It is understood that the controller (not shown) can be the glucometer in certain embodiments.

In use, the patient or user can obtain a blood sample from the patient's fingertip or other site by positioning the distal end of the device 50 against the site and actuating the lancet to pierce the skin, thereby drawing blood. As described above with respect to FIGS. 1, 2A, and 2B, the stimulation component 52 is actuated before or at the same time as the actuation of the lancet to reduce the pain of the skin being pierced. Once the skin has been pierced, the patient or user then touches one end of a standard, commercially-available disposable glucometer test strip onto the blood sample and inserts the other end of the test strip into the glucose test strip receptacle 54. The integrated glucometer (not shown), which is operably coupled to the controller (not shown), processes the blood sample and transmits the results to the display 58, which displays the results for the patient/user.

In addition to providing the glucometer results, the display 58 can also be configured to provide other relevant information. That is, the glucometer is operably coupled to the controller, which can transmit information about the level of stimulation and battery level to be provided on the display. In one embodiment, the display can be any known display such as any display provided on any commercially-available electrical medical device.

In further alternative embodiments, instead of being integrated into an auto lancet, various implementations of the stimulation energy source unit and stimulation component contemplated herein can be integrated into an insulin auto needle injector, an insulin pen, a glucometer device, or any other diabetes treatment device.

FIGS. 4-11 depict another embodiment—a handheld pain reduction device 60 for glucose testing and treatment administration. The device 60 has a body 62, a lancet housing 64, a lancet opening 66 defined in the distal end of the lancet housing 64, a first actuation button 68, a second actuation button 70, and two intensity adjustment buttons 72. In addition, the device 60 has a stimulation energy source unit (schematically depicted as 84) disposed within or associated with the device 60. The stimulation energy source unit 84 is configured to provide electrical and/or vibration energy that can be applied to a patient during use of the device 60 to reduce or eliminate the pain of blood glucose testing.

It is understood that the various components described herein with respect to FIGS. 4-11 can have the same functionality as those components in the embodiments described above and depicted in FIGS. 1-3. Further, various embodiments of the device 60 can also have a testing strip and glucometer, a display, or any other additional component and related functionality as described above with respect to FIGS. 1-3.

Figure 4:
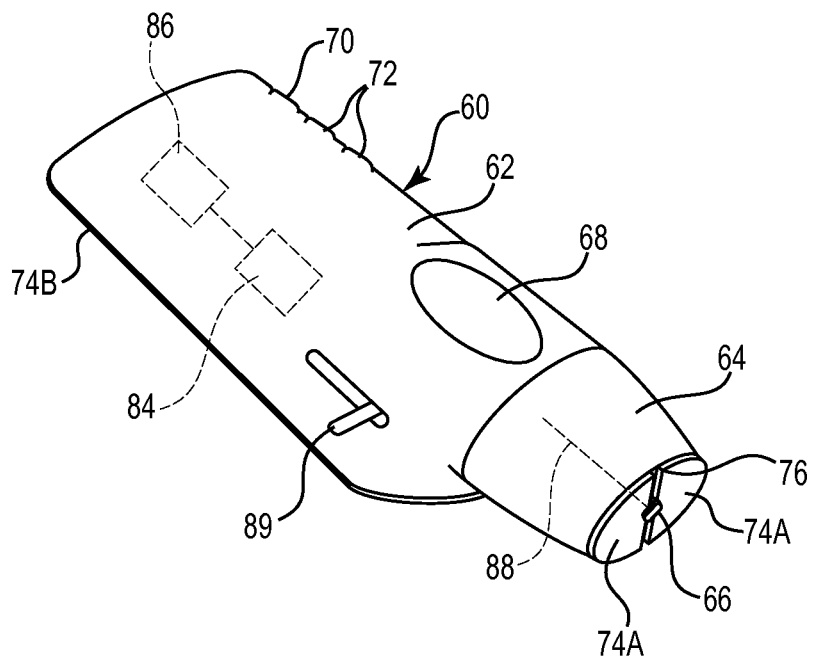
FIG. 4 is a perspective view of a pain reduction device, according to another embodiment.
Figure 5:
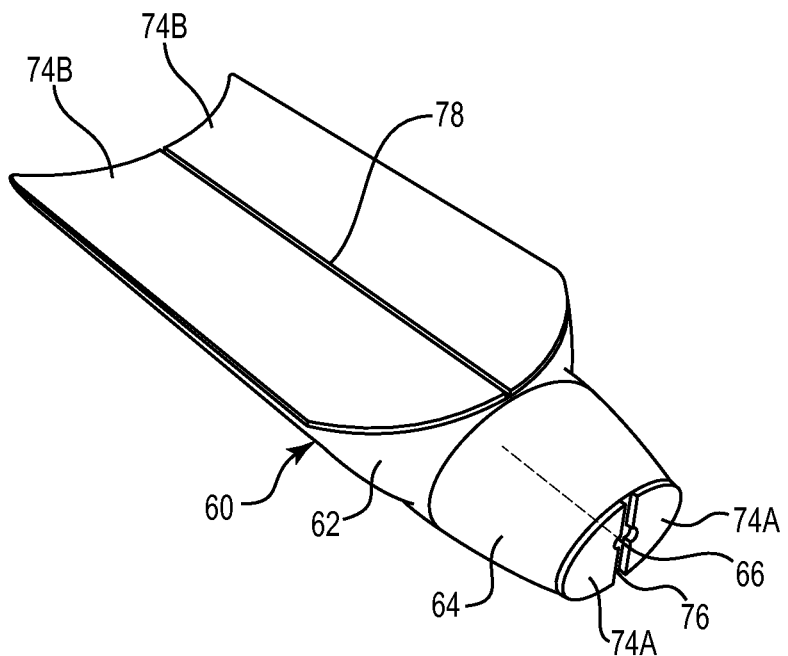
FIG. 5 is a perspective view of the underside of the device of FIG. 4, according to one embodiment.

As best shown in FIGS. 4 and 5, the device 60 also has two stimulation components 74A, 74B operably coupled to the stimulation energy source unit 84. The first stimulation component 74A is disposed on the distal end of the body 62, as best shown in FIG. 4. More specifically, the first stimulation component 74A in this embodiment is the entire face 76 of the distal end of the lancet housing 64 encircling and defining the lancet opening 66. In one implementation, the first stimulation component 74A being the entire face 76 of the distal end of the housing 64 maximizes the surface area of the stimulation component 74A, thereby maximizing the delivery of stimulation, resulting in the most efficient delivery of either electrical or vibration stimulation or both. Alternatively, the first stimulation component 74A comprises a portion of the face 76 of the distal end of the lancet housing 64. The second stimulation component 74B is disposed on the underside 78 of the device 62, as best shown in FIG. 5. More specifically, the second stimulation component 74B is the entire underside 78 of the device 62. Alternatively, the second stimulation component 74B comprises a portion of the entire underside 78 of the body 62.

The device 60 also has a lancet 88 disposed within the lancet housing 64. According to one embodiment, the lancet 88 is movable between a retracted position within the lancet housing 64 and a deployed position in which a distal portion of the lancet 88 protrudes out of the distal end of the lancet housing 64 through the lancet opening 66 and the first stimulation component 74A. Like the embodiment depicted in FIG. 1, in certain implementations, the lancet 88 is structurally similar to commercially-available lancets used on many known, commercially-available auto lancet devices, such that commercially-available lancets can be used with the current embodiment. Alternatively, certain embodiments of the lancet 88 and the device 60 can have a unique configuration such that the lancet 88 is configured to fit solely within devices 60 having the matching unique configuration, thereby providing for specifically dedicated lancets for specific devices 60. In a further alternative, the device 60 is configured such that it will not operate unless the appropriate lancet 88 is used. For example, the lancet 88 can have a unique configuration that matches the unique configuration of the device 60 such that insertion of the lancet 88 results in the device 60 being operable. In one such example, the lancet 88 can have an electrically conductive component such that when the lancet 88 is properly installed into the device 60, the electrically conductive component contacts an appropriate portion of the device 60, thereby closing a circuit that renders the device 60 operable. Alternatively, the lancet 88 can have any unique configuration that, when installed in the device 60 with the matching configuration, results in the closing of a circuit to render the device 60 operable. In one embodiment, this feature can prevent the use of other brands of lancets.

In certain implementations, the lancet housing 64 is a removable lancet housing 64 that is removably coupled to the body 62. In these implementations, the housing 64 can be removed to install or replace a lancet 88. It is understood that the housing 64 can be removably coupled to the body 62 in any known fashion using any known coupling structure. For example, in one embodiment, a proximal portion of the housing 64 has threads, and the distal portion of the body 62 has matching threads such that the housing 64 can be threaded onto the body 62. In an alternative embodiment, the device 60 and housing 64 are configured such that the device 60 will not operate unless the appropriate housing 64 is used. For example, the housing 64 can have a unique configuration that matches the unique configuration of the device 60 such that the coupling of the housing 64 to the device 60 results in the device 60 being operable. In one such example, the housing 64 can have an electrically conductive component such that when the housing 64 is properly coupled to the device 60, the electrically conductive component contacts an appropriate portion of the device 60, thereby closing a circuit that renders the device 60 operable. Alternatively, the housing 64 can have any unique configuration that, when coupled to the device 60 with the matching configuration, results in the closing of a circuit to render the device 60 operable. In one embodiment, this feature can prevent the use of other housings.

In certain embodiments, the device 60 can also have a controller (schematically depicted as 86)—similar to the controller embodiments described above—disposed within the body 62 to control the delivery of stimulation to the patient and, in some embodiments, to control the lancet 88 as well. In one embodiment, the controller 86 is coupled to any buttons, such as buttons 68, 70, 72 and further is coupled to both the stimulation energy source unit 84 and the lancet 88. It is understood that this controller 86 can have all of the same functionality as that described above with respect to FIGS. 1-3.

In one embodiment, the controller 86 can be pre-programmed to gradually increase either electrical or vibration stimulation or both from a predetermined minimal level to a predetermined maximum level, thereby preventing an initial surprise associated with a more sudden application of full electrical and/or vibration stimulation.

In a further embodiment, the controller 86 can be coupled to the actuation buttons 68, 70, the intensity level buttons 72, and any other buttons and can be programmed to deliver varying levels of electrical or vibration stimulation or both to either stimulation component 74A, 74B or both based on patient input via the intensity level buttons 72 or any other buttons. For example, the patient in one embodiment can control the level of stimulation to either stimulation component 74A, 74B or both based on the amount that the actuation buttons 68, 70 are depressed. This transmits a signal to the controller 86 that results in actuation of the stimulation energy source unit 84 to generate the corresponding level of stimulation. Further, the patient/user can adjust the intensity of the stimulation delivered to the skin by the second stimulation component 74B using the intensity level buttons 72. In a further embodiment, the two intensity buttons 72 can also be operably coupled to the first stimulation component 74A such that the buttons 72 can be used by the patient/user to adjust the intensity of the stimulation delivered by the first stimulation component 74A as well.

According to one embodiment, the first actuation button 68 is operably coupled to the first stimulation component 74A such that actuation of the first actuation button 68 actuates the first stimulation component 74A. In certain implementations, the first actuation button 68 also actuates the lancet 88 to move from its retracted position to its deployed position such that the lancet 88 pierces the patient's skin. In one embodiment, the controller 86 can be programmed to provide for the stimulation energy source unit 84 to be actuated to deliver stimulation to the first stimulation component 74A for some predetermined period prior to actuating the lancet 88 to pierce the skin. Alternatively, the controller 86 can be programmed such that when the user begins to press the button 68, the first stimulation component 74A is actuated, but not the lancet 88. As a specific example, when the button 68 has been depressed less than 50% of the full possible amount it can be depressed, the controller 86 only actuates the stimulation component 74A, and not the lancet 88. Once the button 68 has been depressed more than 50% of the full amount it can be depressed, both the stimulation component 74A and lancet 88 are actuated. Alternatively, any known mechanism can be used for ensuring that the stimulation component 74A is actuated before the lancet 88 pierces the skin. Regardless of the exact configuration, this feature makes it possible for the electrical and/or vibration stimulation to begin to be delivered before the lancet 88 pierces the skin, thereby providing maximum pain reduction.

In this implementation, the second actuation button 70 is operably coupled to the second stimulation component 74B (or via the controller 86 and the stimulation energy source unit 84 to the second stimulation component 74B) such that actuation of the second actuation button 70 actuates the second stimulation component 74B. In yet another embodiment, the device 60 can have separate actuation and intensity buttons for both stimulation components, along with a separate actuation button for actuating the lancet 88. In a further alternative, any configuration of buttons can be provided for purposes of actuation of the components of the device 60.

Figure 7:
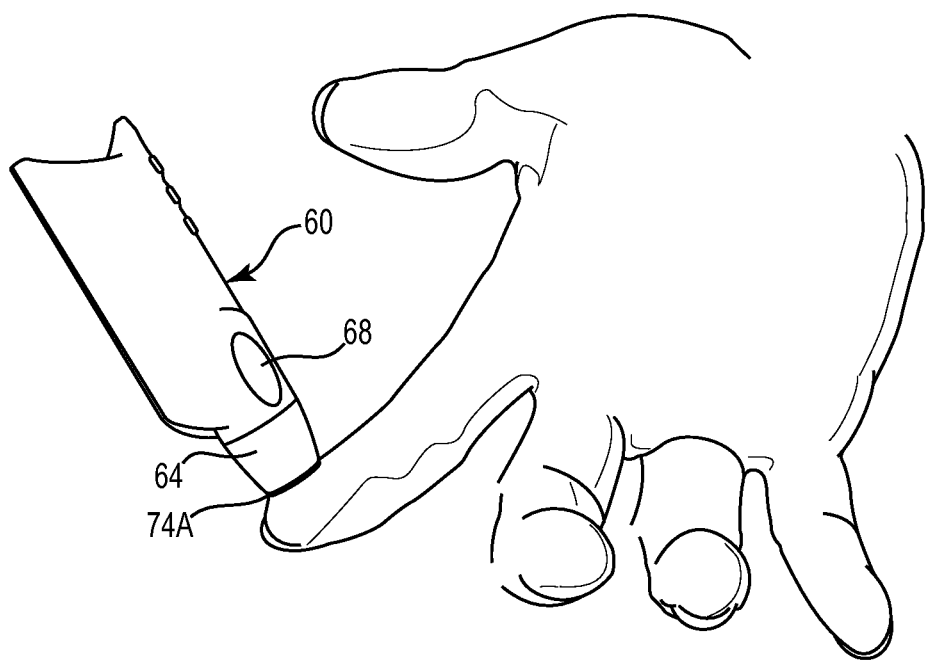
FIG. 7 is a perspective view of the device of FIG. 4 in use drawing blood from a finger, according to one embodiment.
Figure 8:
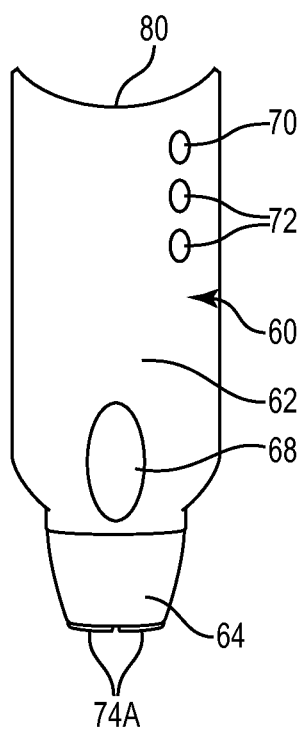
FIG. 8 is a top view of the device of FIG. 4, according to one embodiment.

In use according to certain embodiments as best shown in FIG. 7, the device 60 can be used to perform a blood glucose test by positioning the distal end of the lancet housing 64 against the patient's finger (or elsewhere on the patient) and actuating the first actuation button 68 and thereby actuating the lancet 88 to move into the deployed position and thereby pierce the patient's skin to obtain a blood sample prior to retracting to the retracted position. As described above, the actuation of the button 68 actuates the stimulation energy source unit 84 to begin delivering stimulation energy to the stimulation component 74A on the distal end of the lancet housing 64 before actuation of the lancet 88, thereby delivering pain reduction/elimination stimulation to the patient's skin in the same area to be pierced by the lancet 88 before and during the piercing, thereby reducing or eliminating the pain associated thereto.

Alternatively, the device 60 can be configured to randomly vary the time between actuation of the actuation button 68 and either lancet 88 deployment or actuation of the stimulation component 74A or both. More specifically, the controller 86 can be programmed to provide for the random actuation. According to one embodiment, the random timing acts to reduce the user's apprehension when activating the trigger button and contributes to the reduction of pain sensation.

Figure 6:
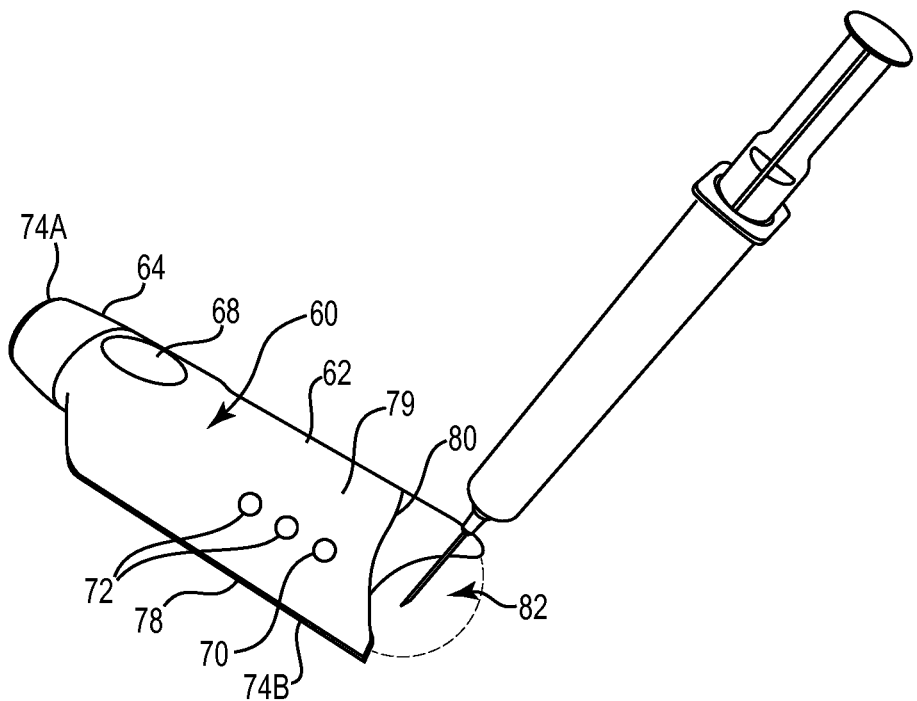
FIG. 6 is a perspective view of the use of the device of FIG. 4 with an insulin needle and syringe, according to one embodiment.
Figure 9:
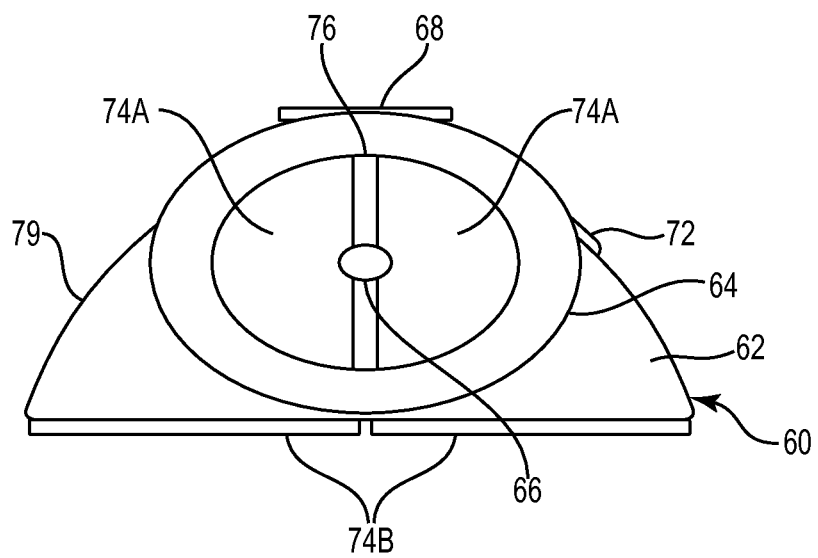
FIG. 9 is a side view of the distal end of the device of FIG. 4, according to one embodiment.
Figure 10:
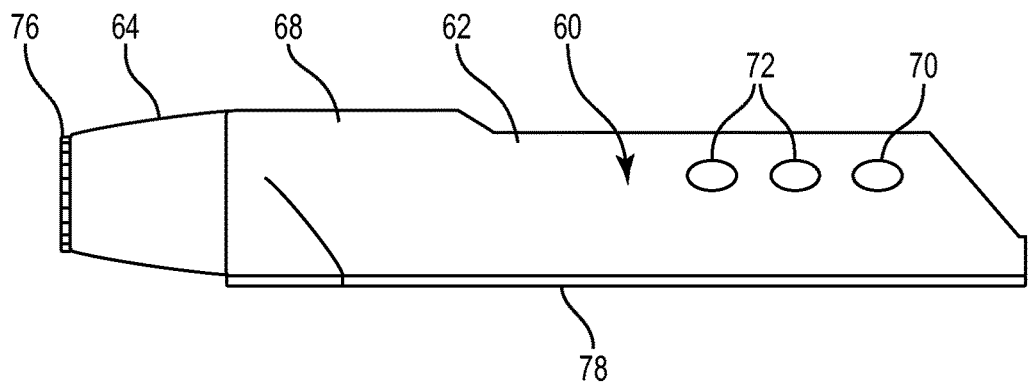
FIG. 10 is a side view of the device of FIG. 4, according to one embodiment.
Figure 11:
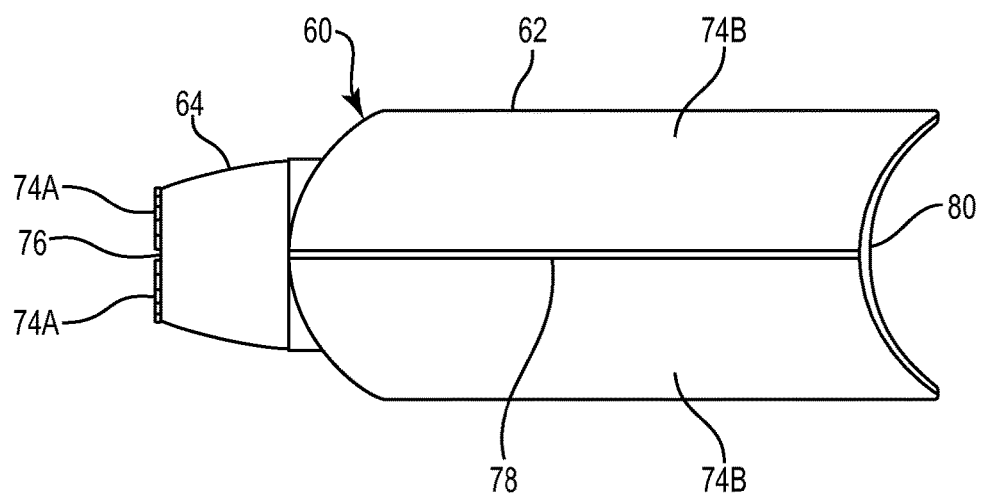
FIG. 11 is a bottom view of the device of FIG. 4, according to one embodiment.

As best shown in FIG. 6, the same device 60 can also be used to reduce or eliminate the pain associated with the diabetes treatment injection, in some cases based on the blood glucose testing previously performed using the same device 60. For this purpose, the patient or other user holds the underside 78 of the device 60 against the patient's skin by grasping the top portion 79 of the device 60. In one embodiment, the top portion 79 of the body 62 has a rounded shape or profile, as best depicted in FIG. 9, configured to be easily grasped by the patient/user. Further, the body 62 in certain embodiments can also have a concave-shaped proximal end 80 as best shown in FIG. 6 that creates an optimal injection site (identified as the area 82 defined by the proximal end 80 of the device 60 and the dotted lines) adjacent to the proximal end 80. That is, the concave-shaped proximal end 80 provides the stimulation energy provided by the stimulation component 74B in the closest possible proximity to the injection device, thereby maximizing the pain reduction/elimination. In one embodiment, the second stimulation component 74B can be actuated by the patient/user pressing the second actuation button 70. Alternatively, the second stimulation component 74B can be actuated by being placed in contact with the skin. More specifically, the second stimulation component 74B is configured to sense that it is in contact with the skin and transmits a signal to the controller 86 or directly to the stimulation energy source unit 84 to actuate the unit to generate stimulation to be delivered to the component 74B. It is understood that any known sensor or sensing technology can be incorporated into the device 60 to incorporate this feature.

According to another embodiment, the rounded shape of the top portion 79 of the body 62 can also allow the patient/user to hold the device 60 down onto skin while at the same time optionally pinching his/her skin at the optimal injection site 82.

In another alternative embodiment, the device 60 can also be configured to measure the patient's specific skin attributes and utilize that information to deliver the appropriate level of stimulation to the patient based on that information. Certain skin attributes such as resistance and capacitance vary depending on body location, skin moisture, and from person to person. These attributes change the way electrical current passes through the skin layer and can significantly affect the delivery of electrical stimulation along with each individual's sensation of this stimulation. For example, the level of electrical stimulation required to reduce the pain of injection on the thigh may be much different than the levels needed to reduce pain on the abdominal wall. Similarly, the level of electrical stimulation needed to reduce pain on moist skin will vary from the levels required for pain reduction on dry skin. More specifically, the controller 86 as described above can be programmed to control the measurement of the resistance of the skin between two electrically conductive elements on the device 60. For example, in one embodiment, each of the stimulation components 74A, 74B have two electrically conductive elements, and the controller 86 can be used to measure the resistance of the skin between the two elements in either of the components 74A, 75B. That is, either of the components 74A, 75B can be placed into contact with the skin and the controller 86 can control the measurement of the resistance of that skin between the two electrically conductive elements on that component (74A or 74B).

In a specific example, the patient could place the stimulation component 74A against the skin at or near the testing site. The controller 86 can then control the two electrically conductive elements on the component 74A to measure the resistance of the skin at that site. The measurement would be transmitted to the controller 86, which would use that information to identify an appropriate amount of electrical stimulation and transmit the appropriate instructions for actuation to the stimulation component 74A. For example, assuming that the resistance was measured to be 500 Ohms, the controller 86 would use that information to transmit instructions to the stimulation energy source unit 84 to generate 40 mA TENS to the stimulation component 74A. The stimulation can then be fine tuned by the patient/user using the intensity adjustment buttons 72. If the controller 86 measures a higher resistance, then the controller 86 can send signals or instructions to the stimulation energy source unit 84 to deliver a more powerful TENS stimulation. As such, this embodiment provides for a level of stimulation that is automatically targeted towards real time individual skin measurements to prevent the need for large manual adjustments in stimulation levels.

In accordance with another alternative implementation, the device 60 can be configured to have an automatic on/off feature triggered by contact with the skin. More specifically, each of the first and second stimulation components 74A, 74B can be configured to detect when it is in contact with the skin. This detection causes the component 74A, 74B to transmit an electrical or electronic signal to the controller 86, which thereby transmits an actuation signal to the stimulation energy source unit 84 actuating the unit to transmit stimulation energy to the appropriate component 74A, 74B. Subsequently, when the device 60 is removed from the skin, the component 74A, 74B detects the absence of the skin and transmits a signal that results in the stimulation energy source unit 84 being shut off.

In certain embodiments, the device 60 is configured to prevent inadvertent actuation of either stimulation components 74A, 74B. For example, in one embodiment, the device 60 can be configured so that the stimulation component 74A is only functional (capable of being actuated) when the lancet 88 is positioned in the "ready" position (also known as the "cocked" positioned). That is, various embodiments of the device 60 (and the other devices disclosed and depicted in this document) contemplated herein operate similarly to commercially-available auto lancets, wherein such devices have a lever or other actuable component coupled to the lancet 88 such that the user can move the lancet 88 from an untensioned position to a tensioned position prior to actuating the lancet 88 to pierce the patient's skin. In certain embodiments as best shown in FIG. 4, the device 60 has a slidable lever 89 operably coupled to the lancet 88 such that the patient or user can "cock" the lancet 88 (move it from the untensioned position to the tensioned position prior to actuation. In this embodiment, the lancet 88 or the lever 89 can be operably coupled to the controller 86 or alternatively to the stimulation energy source unit 84 such that a signal is transmitted to either the controller 86 or the unit 84 indicating that the lancet 88 is in the cocked position, thereby rendering the stimulation energy source unit 84 and the stimulation component 74A operable for actuation. Similarly, in these embodiments, the device 60 can also be configured such that the stimulation component 74B is only functional when the lancet 88 is in the untensioned or uncocked position. As such, according to one embodiment, the controller 86 is configured to monitor the position of the lancet 88 and is programmed to only allow functionality of the proper stimulation component. In this way, the controller 86 limits stimulation to the area about to be pierced by a lancet 88 or needle injection and reduces the risk of an inadvertent actuation of a stimulation component 74A, 74B.

Figure 12:
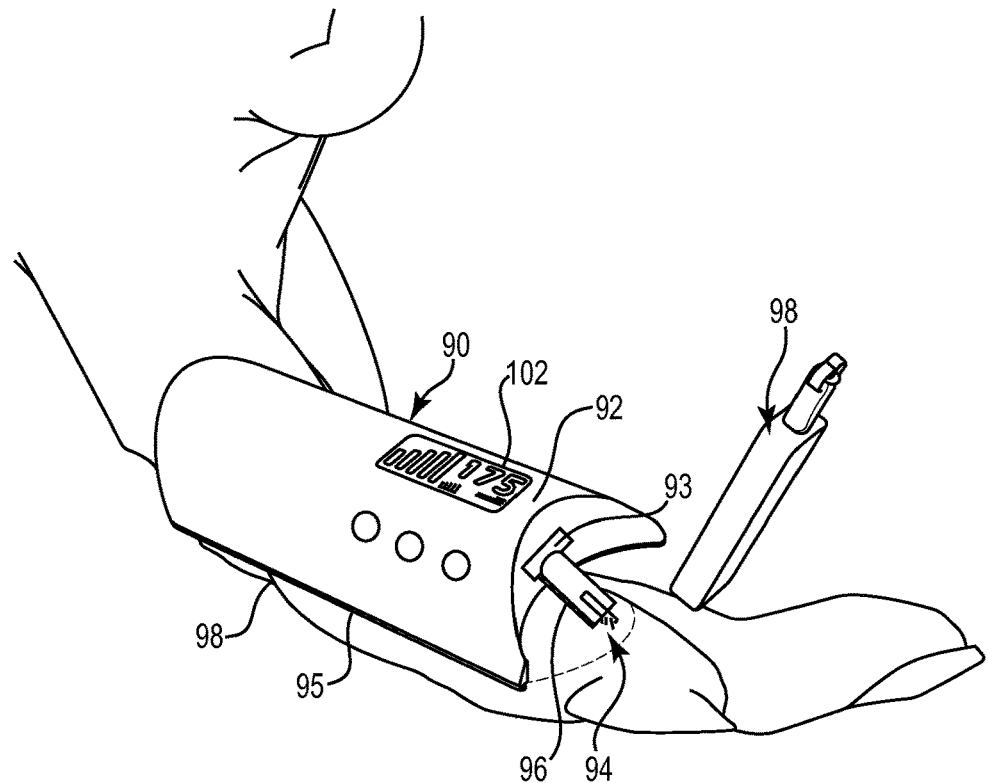
FIG. 12 is a perspective view of a pain reduction device in use during blood glucose testing, according to another embodiment.
Figure 13:
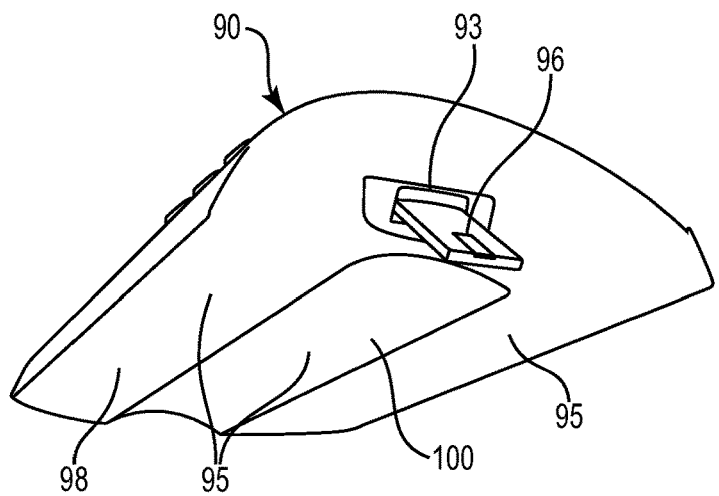
FIG. 13 is a perspective view of the device of FIG. 12, according to one embodiment.

FIGS. 12 and 13 depict a handheld combination blood glucose testing and pain reduction/elimination device 90, according to another embodiment. It is understood that the various components in this device that are similar to the components depicted in FIGS. 1-11 and described above can have the same functionality as those embodiments above. This device 90 has a concave shaped distal portion 92 that creates an optimal testing site 94 similar to the optimal injection site described above. In addition, the device 90 has a stimulation component 95 on the underside 98 of the device 90. Further, in one implementation, the underside 98 has a concave shape 100 as best shown in FIGS. 13 and 16 that allows for improved conduction of electrical and/or vibration stimulation onto a finger by maximizing contact between the stimulation component 95 and the patient's finger. In this way, the digital nerves on either side of the finger can be more fully stimulated, thereby resulting in more complete pain reduction.

In this embodiment, the concave distal end 92 has a glucose test strip receptacle 93 configured to receive a testing strip 96 that is positioned to contact the skin within the optimal testing site 94. The device 90 also has a glucometer (not shown) that is operably coupled to the receptacle 94 and to the display 102. It is understood that the controller (not shown) can be the glucometer in certain embodiments. The device 90 can be used in a fashion similar to that described above with respect to FIG. 3, except that the device 90 has no integral lancet. Instead, the device 90 is configured to be used with any separate, commercially-available lancet device such as the device identified as 98 in FIG. 12.

In use, the device 90 can be positioned on the patient's finger next to the testing site such that the testing site is the same as the optimal testing site 94. Any commercially-available lancet 98 can then be used by the patient to pierce the skin at the optimal testing site 94, and then the device 90 is positioned by the patient/user such that the testing strip 96 contacts the blood. In one embodiment, the device 90 is initially positioned adjacent to the testing site so that, when the lancet has been used to pierce the skin and draw blood, the patient can then simply slide the device 90 distally until the testing strip 96 contacts the blood. The blood is then taken up by the testing strip 96, which is operably coupled to the glucometer. The glucometer tests the blood, and the results are displayed on the display 102. In this way, blood testing can be accomplished with very minimal movement of the device 90 toward the blood sample in the optimal testing site 94 created by the lancet 98. In a further embodiment, the device 90 can also be used to reduce/eliminate pain of an injection by performing the injection in the optimal testing site 94.

Figure 14:
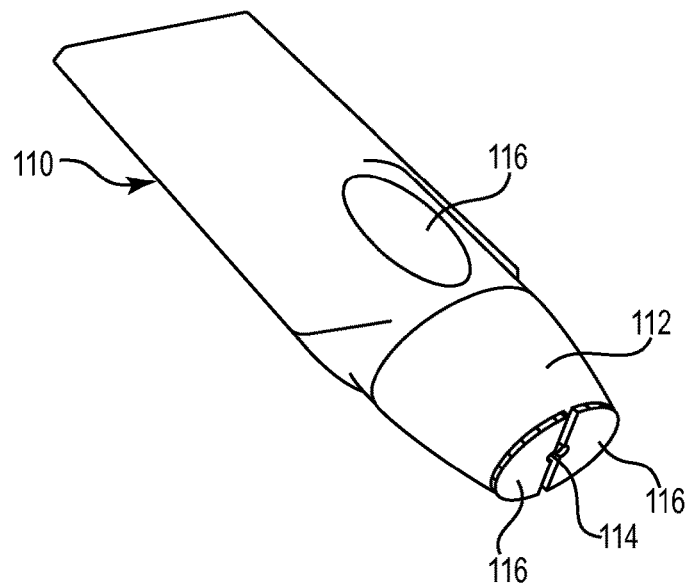
FIG. 14 is a perspective view of a pain reduction device, according to a further embodiment.

FIG. 14 depicts a further alternative embodiment of a combination blood glucose testing and pain reduction/elimination device 110. This device 110 has a stimulation energy source unit (not shown), a controller (not shown), a lancet housing 112 at the distal end of the device 110 that houses a lancet (not shown), and an actuation button 116. The distal end of the housing 112 defines a lancet opening 114 into the lancet housing 112. The lancet (not shown) is configured to move between a retracted position within the housing 112 and a deployed position in which a distal portion of the lancet extends out of the lancet housing 112 through the lancet opening 114. In this embodiment, the distal end of the lancet housing 112 also has a stimulation component 116 that encircles the opening 114. It is understood that the various components of this device 110 can have the same functionality as described above with respect to the other device embodiments.

Figure 15:
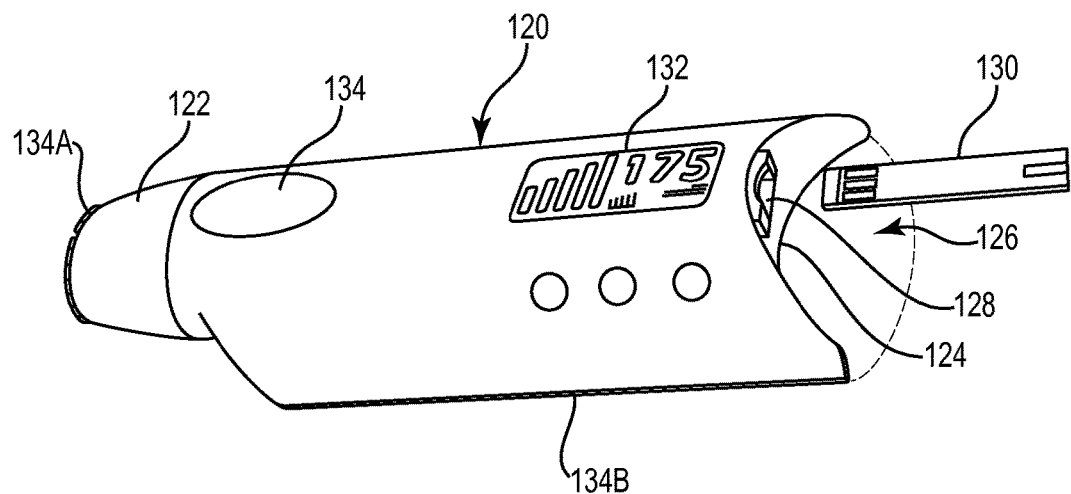
FIG. 15 is a perspective view of a pain reduction device, according to yet another embodiment.

Another embodiment of a combination blood glucose testing and pain reduction/elimination device 120 is depicted in FIG. 15. In addition to a lancet housing 122 containing a lancet (not shown), a stimulation energy source unit (not shown), an actuation button 134, a glucometer (not shown), and a controller (not shown) similar to those described above, this device 120 has a concave proximal end 124 that creates an optimal testing site 126 adjacent to the proximal end 124. Further, the proximal end 124 has a testing strip receiving cavity 128 configured to receive a removable testing strip 130. The testing strip strip receiving cavity 128 is operably coupled to the glucometer and/or the controller, which are operably coupled to a display 132 that displays the results of the test. In this embodiment, the device has two stimulation components, one 134A on the distal end of the lancet housing 122 and one 134B on the underside of the device 120. It is understood that the various components of this device 120 can have the same functionality as described above with respect to the other device embodiments.

Figure 16A:
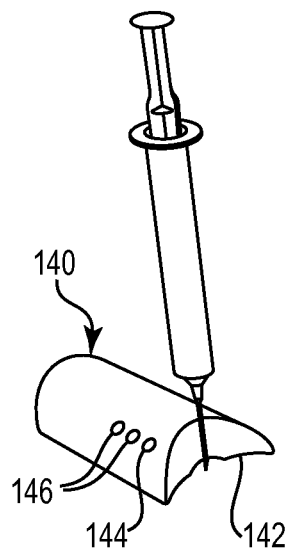
FIG. 16A is a perspective view of a pain reduction device in use, according to another embodiment.
Figure 16B:
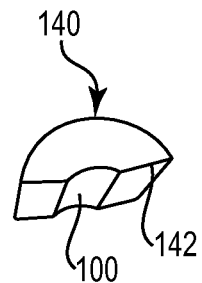
FIG. 16B is a perspective view of the underside of the pain reduction device of FIG. 16A, according to one embodiment.
Figure 16C:
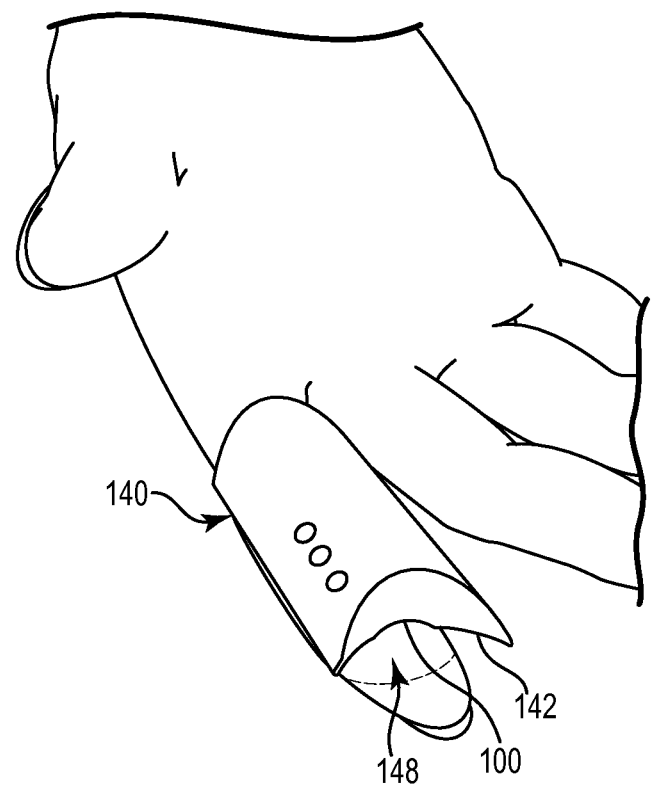
FIG. 16C is a perspective view of the pain reduction device of FIG. 16A in use, according to one embodiment.

FIGS. 16A, 16B, and 16C depict a further embodiment of a pain reduction/elimination device 140 for use with a diabetes treatment injection. This device 140 has a concave distal end 142, an actuation button 144, two intensity level buttons 146, a stimulation energy source unit (not shown), and a controller (not shown). The concave distal end 142 creates an optimal injection site 148 as described above. In use, when an injection becomes necessary, the device 140 can be positioned adjacent to the injection site such that it is the same as the optimal injection site 148, and then the stimulation can be actuated at the same time as or prior to the insertion of the needle into the skin for the injection.

While the preferred embodiment and various alternative embodiments of the invention have been disclosed and described in detail herein, it may be apparent to those skilled in the art that various changes in form and detail may be made therein without departing from the spirit and scope thereof.

What is claimed is:

1. A combination blood testing and pain reduction device, the device comprising:
   (a) a body;
   (b) a lancet housing disposed at a first end of the body, the lancet housing comprising:
      (i) an opening defined in the lancet housing;
      (ii) a first stimulation component disposed on the lancet housing, wherein the first stimulation component comprises a first electrode configured to be capable of delivering at least one of electrical stimulation and vibration stimulation; and
      (iii) a lancet disposed at least partially within the lancet housing;
   (c) a concave-shaped second end of the body, the second end defining a testing site adjacent to the second end;
   (d) a second stimulation component disposed along a bottom portion of the body, wherein the second stimulation component comprises a second electrode configured to be capable of delivering at least one of electrical stimulation and vibration stimulation; and
   (e) a stimulation generating unit disposed within the body, the stimulation generating unit configured to transmit at least one of electrical energy and vibration energy to the first and second stimulation components.

2. The device of claim 1, further comprising a testing strip opening defined in the second end of the body, the testing strip opening configured to receive a testing strip.

3. The device of claim 2, further comprising a testing component operably coupled to the testing strip opening and a display operably coupled to the testing component.

4. The device of claim 1, wherein the body comprises a rounded top portion configured to be easily grasped by a patient.

5. The device of claim 1, wherein the bottom portion of the body comprises a concave shape, wherein the concave shape of the bottom portion is configured to allow the bottom portion to be positioned over a patient's finger such that contact between the stimulation component and the patient's finger is maximized.

6. The device of claim 1, further comprising a controller operably coupled to the stimulation generating unit.

7. The device of claim 6, further comprising a display operably coupled to the controller.

8. The device of claim 6, further comprising at least one actuation button operably coupled to the controller.

9. The combination blood testing and pain reduction device of claim 1, wherein the lancet comprises a retracted position disposed within the lancet housing and a deployed position wherein at least a distal portion of the lancet extends out of the lancet housing through the opening.

10. The device of claim 1, further comprising at least one actuation button disposed on the body.

11. The device of claim 1, further comprising at least one intensity adjustment button disposed on the body.

12. The device of claim 1, further comprising a slidable lever operably coupled to the lancet.

13. A combination blood testing and pain reduction system comprising:
   (a) the device of claim 1; and
   (b) a separate lancet configured to pierce skin at the testing site.

14. A method of testing blood and reducing pain relating to the blood testing, the method comprising:
   positioning a pain reduction device on a patient's skin, the pain reduction device comprising:
      (a) a body;
      (b) a lancet housing disposed at a first end of the body, the lancet housing comprising:
         (i) an opening defined in the lancet housing;
         (ii) a first stimulation component disposed on the lancet housing; and
         (iii) a lancet disposed at least partially within the lancet housing;
      (c) a concave-shaped second end of the body, the second end defining an injection site adjacent to the second end;
      (d) a second stimulation component disposed along a bottom portion of the body; and
      (e) a stimulation generating unit disposed within the body, the stimulation generating unit configured to transmit at least one of electrical energy and vibration energy to the first and second stimulation components;
   piercing skin at a testing site with the lancet or a separate lancet;
   actuating the stimulation generating unit to generate at least one of electrical energy and vibration energy to the first stimulation component during the piercing of the skin, thereby reducing the pain of the piercing of the skin;
   injecting insulin at the injection site; and
   actuating the stimulation generating unit to generate at least one of electrical energy and vibration energy to the second stimulation component during the injecting, thereby reducing the pain of the injecting of the insulin.

15. The method of claim 14, wherein the device further comprises a testing strip opening defined in the second end of the body, the testing strip opening configured to receive a testing strip.

16. The method of claim 15, further comprising positioning a testing strip in the testing strip opening.

17. The method of claim 16, further comprising positioning the device such that the testing strip contacts blood forming at the testing/injection site, such that the blood is taken up by the testing strip.

18. The method of claim 17, wherein the positioning the device further comprises advancing the second end toward a target testing area on the patient.

19. The method of claim 14, further comprising measuring skin attributes prior to actuating the stimulation generating unit.

20. The method of claim 19, further comprising controlling an amount of the at least one of electrical energy and vibration energy based on the skin attributes.

21. The method of claim 14, further comprising actuating a button, wherein actuating the button causes the actuating of the stimulation generating unit or the piercing the skin with the lancet or the separate lancet.

22. The method of claim 21, wherein the actuating of the stimulation generating unit is timed randomly in relation to actuating the button.

23. The method of claim 21, wherein the piercing the skin with the lancet or the separate lancet is timed randomly in relation to actuating the button.

24. The method of claim 14, further comprising contacting the patient's skin with one of the first and second stimulation components, wherein the contacting the patient's skin actuates the stimulation generating unit to transmit at least one of electrical energy and vibration energy to the one of the first and second stimulation components.

25. A combination blood testing and pain reduction device, the device comprising:

(a) a body;
(b) a lancet housing disposed at a first end of the body, the lancet housing comprising:
   (i) an opening defined in the lancet housing;
   (ii) a first electrical and vibration stimulation component disposed on the lancet housing; and
   (iii) a lancet disposed at least partially within the lancet housing;
(c) a concave-shaped second end of the body, the second end defining a testing site adjacent to the second end;
(d) a second electrical and vibration stimulation component disposed along a bottom portion of the body;
(e) a stimulation generating unit disposed within the body, the stimulation generating unit configured to transmit at least one of electrical energy and vibration energy to the first and second stimulation components; and
(f) a controller operably coupled to the stimulation generating unit.

26. The device of claim 25, further comprising at least one actuation button operably coupled to the controller.

27. The device of claim 25, further comprising a slidable lever operably coupled to the lancet.

\* \* \* \* \*